United States Patent [19]

Fischer et al.

[11] Patent Number: 5,162,590

[45] Date of Patent: Nov. 10, 1992

[54] VINYL POLYETHER ALCOHOLS

[75] Inventors: Martin Fischer, Ludwigshafen; Richard Baur; Paul Diessel, both of Mutterstadt, all of Fed. Rep. of Germany

[73] Assignee: BASF Aktiengesellschaft, Ludwigshafen, Fed. Rep. of Germany

[21] Appl. No.: 651,958

[22] Filed: Feb. 7, 1991

[30] Foreign Application Priority Data

Feb. 16, 1990 [DE] Fed. Rep. of Germany ....... 4004883

[51] Int. Cl.$^5$ ..................... C07C 43/13; C07C 43/14; C07C 43/178
[52] U.S. Cl. ..................................... 568/622; 568/601
[58] Field of Search ................................ 568/622, 601

[56] References Cited

U.S. PATENT DOCUMENTS

| | | | |
|---|---|---|---|
| 4,375,565 | 3/1983 | Greif et al. | 568/622 |
| 4,399,313 | 8/1983 | Vanderberghe et al. | 568/622 |
| 4,421,168 | 12/1983 | Hurd | 568/622 |
| 4,463,806 | 8/1984 | Hurd | 568/622 |
| 4,474,678 | 10/1984 | Lutz et al. | 568/622 |
| 4,600,523 | 7/1986 | Piorr et al. | 568/622 |
| 4,665,236 | 5/1987 | Edwards | 568/622 |
| 4,925,587 | 5/1990 | Schenker et al. | 568/622 |
| 4,960,952 | 5/1990 | Kemp | 568/622 |

FOREIGN PATENT DOCUMENTS

| | | |
|---|---|---|
| 149173 | 7/1985 | European Pat. Off. |
| 155710 | 9/1985 | European Pat. Off. |
| 174610 | 3/1986 | European Pat. Off. |
| 244841 | 11/1987 | European Pat. Off. |
| 299360 | 1/1989 | European Pat. Off. |
| 2854826 | 6/1979 | Fed. Rep. of Germany |
| 2263235 | 10/1975 | France |

OTHER PUBLICATIONS

Fatent Abstracts of Japan, JP-AS 87/45,851, and JP-A-56 039–032, Apr. 14, 1981.
Technische Information, Jun. 1983, pp. 1–7.

Primary Examiner—Werren B. Lone
Attorney, Agent, or Firm—Oblon, Spivak, McClelland, Maier & Neustadt

[57] ABSTRACT

Vinyl polyether alcohols of formula I $$R-(O-A)_n-O-CH_2-\underset{\underset{OH}{|}}{CH}-CH=CH_2 \quad\quad I$$

($R = C_1$-$C_{25}$-alkyl, $C_2$-$C_{25}$-alkenyl or alkylaryl having a total of not more than 20 carbon atoms,
A = 1,2-alkylene having from 2 to 4 carbon atoms and n = 1 to 20).

These compounds serve as intermediates in the preparation of polyether sulfonates of formula III $$R-(O-A)_n-O-CH_2-\underset{\underset{OH}{|}}{CH}-CH_2-CH_2-SO_3M \quad\quad III$$

(M = hydrogen, alkali metal or ammonium).

The vinyl polyether alcohols of formula I are useful as surface-active compounds for inclusion in surface-active compositions.

3 Claims, No Drawings

VINYL POLYETHER ALCOHOLS

The present invention relates to novel vinyl polyether alcohols of the general formula I $$R-(O-A)_n-O-CH_2-\underset{\underset{OH}{|}}{CH}-CH=CH_2 \qquad I$$

in which
R stands for $C_1$-$C_{25}$-alkyl, $C_2$-$C_{25}$-alkenyl or alkylaryl having a total of not more than 20 carbon atoms,
A denotes a 1,2-alkylene group having from 2 to 4 carbon atoms and
n is a number from 1 to 20,
and to a process for the preparation of the compounds of formula I, to their use as surface-active components of surface-active compositions and to said surface-active compositions.

The present invention further relates to a process for the preparation of polyether sulfonates of the general formula III $$R-(O-A)_n-O-CH_2-\underset{\underset{OH}{|}}{CH}-CH_2-CH_2-SO_3M, \qquad III$$

in which M denotes hydrogen, an alkali metal or ammonium, from said vinyl polyether alcohols I and to the use of compounds III as surface-active components in detergent, cleaning and cosmetic preparations and to said preparations.

Polyglycol ether sulfonates, such as are described in DE-A 3,735,056 (1) for example, are important surface-active compounds which are used as surfactants in a wide variety of industrial applications. Usual methods of making such compounds include, for example, the chlorination of appropriate polyglycol ether alcohols with agents such as thionyl chloride or phosgene followed by reaction with alkali metal sulfites. This procedure is complicated and, furthermore, gives rise to problems relating to corrosion, waste disposal and toxicity. Thus novel, simpler methods for the synthesis of such polyether sulfonates are particularly welcome, especially when the resulting polyether sulfonate molecule additionally contains functional groups, such as hydroxyl, in a vicinal position to the sulfonate group.

The use of vinyl oxirane as a synthesis unit for the preparation of hydroxy-hydrocarbyl ethers from alcohols or phenols and epoxides has been described in JP-AS 87/45,851 (2), for example.

Polyether sulfonates III are recommended for use as auxiliaries in methods of tapping crude oil from underground reservoirs in specifications DE-A 2,854,826 (3), U.S. Pat. No. 4,421,168 (4) and U.S. Pat. No. 4,463,806 (5).

Polyether sulfates, as described in Technische Information TI/P 2759d, June 1983 (6) in a discussion on Lutensit ®-AS brands of BASF Aktiengesellschaft, are frequently used as surfactants in detergent, cleaning and cosmetic preparations.

It is an object of the present invention to provide a simple and efficient method of synthesizing polyether sulfonates III.

Accordingly, we have found the vinyl polyether alcohols I defined above, which act as intermediates in the synthesis of polyether sulfonates III and which constitute per se surface-active compounds having valuable properties for industrial applications.

The vinyl polyether alcohols I contain a hydrophobic radical R consisting of a straight-chain or branched-chain $C_1$-$C_{25}$-alkyl group, a straight-chain or branched-chain $C_2$-$C_{25}$-alkenyl group or an alkylaryl group containing a total of not more than 20 carbon atoms.

Examples of $C_1$-$C_{25}$-alkyl groups are methyl, ethyl, propyl, butyl, hexyl, octyl, isooctyl, 2-ethylhexyl, nonyl, isononyl, decyl, undecyl, dodecyl, tridecyl, isotridecyl, myristyl, cetyl, stearyl, and eicosyl.

Examples of $C_2$-$C_{25}$-alkenyl groups are vinyl, 1-propenyl, 2-propenyl, oleyl, linolyl, and linolenyl.

Examples of alkylaryl groups having a total of not more than 20 carbon atoms are tolyl, methylnaphthyl, xylyl, mesityl, cumyl, ethylphenyl, propylphenyl, butylphenyl, hexylphenyl, octylphenyl, 2-ethylhexylphenyl, nonylphenyl, decylphenyl, dodecylphenyl and myristylphenyl. The substituents on the aromatic ring system may be in any position.

Preferred compounds I are those in which R stands for a relatively long-chain alkyl group, in particular a $C_8$-$C_{20}$-alkyl group. Such radicals R are based, for example, on natural fatty alcohols or synthesized alcohols, of which the latter are normally produced by oxo synthesis or Ziegler synthesis, in which case they are generally a mixture of various isomers and adjacent homologs, for example $C_9$/$C_{11}$- or $C_{13}$/$C_{15}$-oxo-alcohols and $C_8$/$C_{10}$-, $C_{12}$/$C_{14}$- or $C_{10}$/$C_{20}$-Ziegler-alcohols.

The 1,2-alkylene group A particularly stands for an ethylene group but may also denote a propylene, 1,2-butylene or 2,3-butylene group.

The degree of alkoxylation n is between 1 and 20, preferably between 2 and 15 and more preferably between 3 and 10. The value of n is usually an average value.

The vinyl polyether alcohols I are advantageously prepared by reacting a polyether alcohol of the general formula II $$R-(O-A)_n-OH \qquad II$$

with vinyl oxirane in the presence of a base.

The base used is generally an alkali metal or alkaline earth metal hydroxide, such as sodium hydroxide, potassium hydroxide, calcium hydroxide or barium hydroxide or an alcoholate of a low-boiling alcohol, such as sodium methylate, sodium ethylate or potassium t-butylate. Catalytic amounts are used, for example from 0.1 to 5% molar, based on II. In the case of higher-boiling alcohols II it is advantageous to distill off any solvent introduced with the base, e.g. water or alcohol, prior to carrying out the reaction with vinyl oxirane.

The reaction with vinyl oxirane is usually carried out at a temperature of from 50° to 180° C. and preferably from 100° to 160° C., at atmospheric pressure or an elevated pressure of up to about 10 bar. The alcohol II may be heated to the desired reaction temperature in admixture with the vinyl oxirane and base, or the vinyl oxirane may be metered to the heated reaction mixture, in which latter case the removal of the heat of reaction is less difficult to control.

For each mole of alcohol II there will generally be used from 1 to 2 moles, preferably from 1 to 1.5 moles, of vinyl oxirane. Any residues of unconverted vinyl oxirane may be distilled off or removed by stripping with an inert gas such as nitrogen.

Alternatively, the reaction between II and vinyl oxirane may be carried out in the presence of a solvent which is inert to vinyl oxirane and alkali, examples thereof being tetrahydrofuran, methyl-t-butyl ether, dioxane, toluene and xylene.

The reaction between II and vinyl oxirane may be carried out batchwise or continuously in a cascade of stirred vessels or in a tubular reactor.

The invention further relates to a process for the preparation of polyether sulfonates III from vinyl polyether alcohols I by reacting a compound I with an alkali metal sulfite, bisulfite or disulfite or ammonium sulfite, bisulfite or disulfite or a mixture thereof. The alkali metals involved are predominantly sodium and potassium.

Particularly suitable compounds for this reaction are alkali metal bisulfites such as sodium or potassium bisulfite, for example in the form of a commercial solution, or mixtures of alkali metal bisulfites with alkali metal sulfites. If the reaction is carried out in the presence of atmospheric oxygen, a portion of the bisulfite will be oxidized to bisulfate, which reacts with sulfite to be reconverted to bisulfite. In this way, use may also be made of sulfite, which is less reactive under normal reaction conditions, to effect addition thereof to I. In this case, the molar ratio of sulfite to bisulfite is advantageously from about 1:2.5 to about 1:1.

The said sulfite addition is usually carried out at a temperature of from 20° to 130° C. and preferably from 50° to 100° C., at atmospheric or slightly elevated pressure (up to about 2 bar). The reaction may be accelerated by adding a free-radical starter, for example an organic peroxide, e.g. dibenzyl peroxide, or an azo compound such as azodiisobutyronitrile or a water-soluble peroxo compound such as potassium peroxo disulfate, or by bubbling air through the reaction mixture.

A high reaction rate is achieved, for example, by at least partially dissolving the vinyl compound I and the sulfite, bisulfite or disulfite in the reaction medium. A suitable solubilizer for this purpose is, in particular, water or a water-miscible alcohol such as methanol, ethanol, n-propanol, isopropanol, n-butanol, s-butanol and t-butanol.

For each mole of I there will generally be used from 1 to 3 moles, preferably from 1 to 1.5 moles, of sulfite, bisulfite, disulfite or mixture thereof.

Under the conditions used, the sulfite addition takes from 1 to 10 hours, in exceptional cases up to 50 hours. Completion of the reaction may be ascertained from redox titration findings, after which any precipitated salt is removed by filtration, and water and any solvent are distilled off. The polyether sulfonate III is thus obtained as a viscous to pasty substance. If it is desired to prepare the free sulfonic acid, it will be necessary to react the said salt with an acid.

In a preferred embodiment, the two reaction stages - the reaction of a polyether alcohol II with vinyl oxirane to form a vinyl polyether alcohol I and the addition of sulfite to said compound I - are combined to form an overall process for the preparation of a polyether sulfonate III, which combined process is particularly significant economically, since it is not necessary to purify the intermediate I, which can be further reacted in situ.

The vinyl polyether alcohols I of the invention have surface-active properties and are thus suitable for a variety of industrial applications. Possible fields of use include, for example, detergents and cleaners for domestic and industrial applications, electroplating, the photographic industry, the textile industry, the paper industry, oil production, the pharmaceutical industry, the cosmetic industry, the food industry and plant nutrition.

The present invention also relates to surface-active compositions containing from 1 to 50% w/w, preferably 1 to 30% w/w, of a vinyl polyether alcohol I or a mixture of said vinyl polyether alcohols acting as surface-active ingredient and also containing conventional auxiliaries and possibly other conventional surfactants.

The polyether sulfonates III are surface-active compounds useful for inclusion in detergents, cleaners and cosmetic preparations.

The present invention further relates to detergents, cleaners and cosmetic preparations containing from 1 to 50% w/w, preferably 5 to 45% w/w, of a polyether sulfonate III or a mixture of said polyether sulfonates.

The cosmetic preparations containing at least one compound III as emulsifier are for example skin creams, lotions, gels skin oils or shampoos, and these may contain other ingredients such as cosmetic oils, conventional emulsifiers, light stabilizers, preservatives, scents and other conventional adjuvants.

The present invention reveals a simple and economically attractive method of manufacturing said polyether sulfonates III from commercially readily available starting products, which method is substantially free from the toxicological, environmental and disposal problems characteristic of conventional synthesis methods.

The polyether sulfonates III are particularly useful for inclusion in detergents, cleaners and cosmetics by virtue of their favorable surfactant properties, particularly their good resistance to hard water and their high degree of stability of saponification under alkaline and weakly acid conditions.

SYNTHESIS EXAMPLES

Example 1

174 g (0.4 mole) of a $C_{13}/C_{15}$-oxo-alcohol which had been reacted with 5 moles of ethylene oxide, were mixed with 2.4 g of a 30% w/w methanolic sodium methylate solution (corresponding to 13 mmoles of $NaOCH_3$), and methanol was distilled off at 60° C. and 30 mbar. The mixture was then kept at a temperature of from 138° to 140° C. for 3.5 hours while 31 g (0.44 mole) of vinyl oxirane were metered thereto. There were obtained 206 g of vinyl polyether alcohol, this constituting a yield of 100%. The iodine number following hydrogenation was 50, and the cloud point was 52° C., as measured according to DIN 53,917.

The vinyl polyether alcohol thus obtained was dissolved in a mixture of 335 ml of ethanol and 130 ml of water at room temperature. Air was bubbled through the solution while a solution of 30.3 g (0.29 mole) of sodium bisulfite and 17.8 g (0.14 mole) of sodium sulfite in 80 ml of water was added dropwise over a period of 2 hours. Stirring was continued for 1 hour at room temperature and for 2 hours under reflux. Following the removal of water and ethanol by distillation at 60° C. and 20 mbar there remained 254 g of polyether sulfonate as a viscous oil. The yield was 100%. 1 g of the sulfonate gave a clear solution in 100 ml of water.

Example 2

Following the procedure described in Example 1, 138 g (0.4 mole) of a $C_{13}/C_{15}$-oxo-alcohol which had been reacted with 3 moles of ethylene oxide were converted to the corresponding polyether sulfonate. There were obtained 218 g of product as a pasty substance, this constituting a yield of 100%.

Example 3

Following the procedure described in Example 1, 116 g (0.4 mole) of a $C_{10}$-oxo-alcohol which had been reacted with 3 moles of ethylene oxide were converted to the corresponding polyether sulfonate. There were obtained 196 g of product as a yellow paste, this constituting a yield of 100%.

Example 4

Following the procedure described in Example 1, 129 g (0.4 mole) of a $C_{13}$-oxo-alcohol which had been reacted with 3 moles of ethylene oxide were converted to the corresponding polyether sulfonate. There were obtained 208 g of product as a light brown paste, this constituting a yield of 100%.

Example 5

Following the procedure described in Example 1, 164 g (0.4 mole) of a $C_{13}$-oxo-alcohol which had been reacted with 5 moles of ethylene oxide were converted to the corresponding polyether sulfonate. There were obtained 243 g of product as a brown paste, this constituting a yield of 100%.

APPLICATION TESTS

A. Basic surfactant data

The vinyl polyether alcohols I and polyether sulfonates III were tested for useful properties as regards the surface tension, foamability and wetting power of aqueous compositions containing the products obtained in Examples 1 to 5.

The surface tension was determined as specified in DIN 53,914. This test measures the force required, in mN/m, to pull a horizontally suspended ring or U-shaped wire from the surface of the liquid.

The foamability was determined as specified in DIN 53,902 by measuring the volume of foam, in ml, one minute after foam-generating agitation had ceased.

The wetting power was determined as specified in DIN 53,901 by submerging a piece of cotton fabric in the surfactant solution under test. This test measures the time taken, in seconds, for the fabric to lose its buoyancy (as caused by air enclosure) and to begin to sink. The shorter the time, the greater the wetting power.

Table 1 below lists the results obtained with the products from Examples 1 to 5. In each case, the surface tension was measured on an aqueous solution containing 0.1 g of anhydrous active ingredient per liter, while the wetting power was determined using an aqueous solution containing 1.0 g of anhydrous active ingredient per liter.

TABLE 1

Surface tension, foamability and wetting power of vinyl polyether alcohols and polyether sulfonates

| Product | Surface tension at 20° C. [mN/m] | Foamability [ml] | Wetting power at 25° C. [sec] |
| --- | --- | --- | --- |
| Vinyl polyether alcohol of Example 1 | 28.8 | 20 | 200 |
| Polyether sulfonate of | | | |
| Example 1 | 28.4 | 170 | 35 |
| Example 2 | 33.2 | 120 | 125 |
| Example 3 | 34.7 | 110 | 187 |
| Example 4 | 28.8 | 200 | 21 |
| Example 5 | 28.1 | 400 | 16 |
| For comparison: | | | |
| Polyether sulfate* | 42.1 | >800 | 45 |

*having the formula $C_{12}H_{25}/C_{14}H_{29}$—O—$(CH_2CH_2O)_{2.5}$—$SO_3Na$ as described in (6)

It is seen from Table 1 above that the vinyl polyether alcohols and polyether sulfonates show an advantageous reduction of surface tension and a marked drop in foaming propensity, which is an advantage in all industrial cleaning processes involving high mechanical agitation. The wetting power of the tested products is in some cases better, and in others poorer, than that of the prior art product, depending on the length of the ethylene oxide chain and on the alcohol radical.

B. Washing efficiency

The primary washing efficiency (dirt removal) was determined by laundering various soiled fabrics in test detergent formulations containing the polyether sulfonates. An increase in reflectance value (whiteness) indicates an improvement in the primary washing effect.

The test washes were conducted in an Atlas Launder-O-meter.

The washing conditions were as follows:

| | |
| --- | --- |
| Number of tests per fabric: | 3 |
| Temperature: | 60° C. and 30° C. |
| Water hardness: | 16.8° dH ≈ 3 mmoles/l (Ca:Mg = 4:1) |
| Duration of wash: | 30 minutes |
| Detergent concentration: | 5 g/l |
| Liquor ratio: | 1:25 |
| Soiled fabrics: | WFK 10 D [Test fabric standardized by the Wäschereiforschung Krefeld (Laundry Research Institute, Krefeld), soiled with a mixture of skin grease and pigment] |
| | EMPA 104 [Test fabric standardized by the Eidgenössische Materialprüfanstalt St. Gallen (Confederate Material Testing Laboratory, St. Gallen), soiled with a mixture of mineral oil and pigment] |

The detergents were formulated as follows:
30% of polyether sulfonate as obtained in Examples 1 to 5, as surfactant,
15% of potassium coconut soap,
1% of polypropylene glycol (molar mass 600),
1% of ethanol and
water to make 100%.

The reflectance values of the soiled fabrics were measured with a Zeiss Elrepho.

Table 2 below lists the test results. The findings show that primary washing efficiency of the polyether sulfonates is in some cases distinctly better than that of the prior art products.

TABLE 2

Washing efficiency of polyether sulfonates

| Product | Primary washing efficiency in % reflectance | | | |
|---|---|---|---|---|
| | Fabric WFK 10 D | | Fabric EMPA 104 | |
| | 60° C. | 30° C. | 60° C. | 30° C. |
| of Example 1 | 59.7 | 59.2 | 24.7 | 19.9 |
| of Example 2 | 64.7 | 59.2 | 23.7 | 19.2 |
| of Example 3 | 51.6 | 49.6 | 19.4 | 15.0 |
| of Example 4 | 63.7 | 58.8 | 22.2 | 18.5 |
| of Example 5 | 60.9 | 58.6 | 24.6 | 19.6 |
| for comparison: | | | | |
| polyether sulfate* | 57.4 | 55.2 | 22.1 | 17.7 |
| polyether sulfonate** free from hydroxyl groups | 52.4 | 48.4 | 19.0 | 16.5 |
| prelaundering reference values | 45.0 | 45.0 | 12.9 | 12.9 |

*having the formula $C_{12}H_{25}/C_{14}H_{29}-O-(CH_2CH_2O)_{2.5}-SO_3Na$ as described in (6)

**having the formula $C_{10}H_{21}-O-(CH_2CH_2O)_3-CH_2CH_2SO_3Na$ as described in (1)

We claim:

1. A vinyl polyether alcohol of the formula I $$R-(O-A)_n-O-CH_2-\underset{\underset{OH}{|}}{CH}-CH=CH_2 \qquad I$$

in which

R stands for $C_1$-$C_{25}$-alkyl, $C_2$-$C_{25}$-alkenyl or alkylaryl having a total of not more than 20 carbon atoms, A denotes a 1,2-alkylene group having from 2 to 4 carbon atoms and n is a number from 1 to 20.

2. A vinyl polyether alcohol of formula I as claimed in claim 1, wherein

R stands for $C_8$-$C_{20}$-alkyl,

A denotes a 1,2-ethylene group and n is a number from 2 to 15.

3. A surface-active formulation containing, as surface-active ingredient, from 1 to 50% w/w of a vinyl polyether alcohol of formula I as claimed in claim 1.

* * * * *